(12) United States Patent
Zierhofer

(10) Patent No.: US 8,880,194 B2
(45) Date of Patent: *Nov. 4, 2014

(54) ELECTRICAL NERVE STIMULATION WITH BROAD BAND LOW FREQUENCY FILTER

(71) Applicant: MED-EL Elektromedizinische Geraete GmbH, Innsbruck (AT)

(72) Inventor: Clemens M. Zierhofer, Kundl (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

This patent is subject to a terminal disclaimer.

(21) Appl. No.: 14/108,796

(22) Filed: Dec. 17, 2013

(65) Prior Publication Data
US 2014/0107730 A1    Apr. 17, 2014

Related U.S. Application Data

(63) Continuation of application No. 12/171,857, filed on Jul. 11, 2008, now Pat. No. 8,639,359.

(60) Provisional application No. 60/949,649, filed on Jul. 13, 2007.

(51) Int. Cl.
| A61N 1/18 | (2006.01) |
| A61N 1/36 | (2006.01) |
| G10L 21/06 | (2013.01) |
| G10L 25/18 | (2013.01) |

(52) U.S. Cl.
CPC ....... *A61N 1/36032* (2013.01); *G10L 2021/065* (2013.01); *G10L 25/18* (2013.01)
USPC ............................................. 607/137; 607/57

(58) Field of Classification Search
USPC ............................................. 607/55, 56, 137
See application file for complete search history.

(56) References Cited

U.S. PATENT DOCUMENTS

| 4,536,844 A | 8/1985 | Lyon ............................. 364/487 |
| 5,271,397 A * | 12/1993 | Seligman et al. ............. 607/137 |

(Continued)

FOREIGN PATENT DOCUMENTS

WO    WO 2009/126680    10/2009    ............. H04R 25/00

OTHER PUBLICATIONS

"9th International Conference on Cochlear Implants and Related Sciences," *Wiener Medizinische Wochenschrift*, Springer-Verlag, vol. 156, No. 119, pp. 1-192, Jun. 2006.

(Continued)

*Primary Examiner* — Carl H Layno
*Assistant Examiner* — Jon Eric C Morales
(74) *Attorney, Agent, or Firm* — Sunstein Kann Murphy & Timbers LLP

(57) ABSTRACT

A system and method of generating electrode stimulation signals for an implanted multi-channel electrode array of a cochlear implant includes processing an acoustic audio signal with a bank of filters. Each filter in the bank of filters is associated with at least one channel having an electrode. The bank of filters includes a first band pass filter that produces a broadband signal b(t) with frequencies that substantially cover at least one of a pitch frequency range of 100 Hz to 400 Hz and a first format range of 400 Hz-1000 Hz. At least one electrode associated with the first band pass filter is activated with electrode stimulation signals based, at least in part, on the broadband signal b(t). The filter bank may include at least one electrode associated with one or more filters other than the first band pass filter, the one or more filters producing signals having only higher frequencies than broadband signal b(t).

28 Claims, 3 Drawing Sheets

First Trace: Broadband signal b(t), band pass filtered within [100 Hz - 400 Hz]

Second Trace: Half wave rectified version of b(t)

(56) References Cited

U.S. PATENT DOCUMENTS

| | | | |
|---|---|---|---|
| 5,749,912 A | 5/1998 | Zhang et al. | 607/57 |
| 6,594,525 B1 | 7/2003 | Zierhofer | 607/57 |
| 7,139,403 B2 | 11/2006 | Richardson et al. | 381/107 |
| 7,225,027 B2 | 5/2007 | Zeng et al. | 607/57 |
| 7,231,257 B2 | 6/2007 | McDermott et al. | 607/57 |
| 7,283,876 B2 | 10/2007 | Zierhofer | 607/57 |
| 7,317,945 B2 | 1/2008 | Litvak et al. | 607/57 |
| 7,542,806 B1 | 6/2009 | Voelkel | 607/56 |
| 8,639,359 B2 | 1/2014 | Zierhofer | 607/137 |
| 2005/0203590 A1* | 9/2005 | Zierhofer | 607/57 |
| 2006/0052841 A1 | 3/2006 | Daly et al. | 607/57 |
| 2006/0080087 A1 | 4/2006 | Vandali et al. | 704/207 |
| 2006/0227986 A1 | 10/2006 | Swanson et al. | 381/312 |
| 2009/0254150 A1 | 10/2009 | Zierhofer | 607/57 |
| 2010/0070000 A1 | 3/2010 | Litvak et al. | 607/57 |

OTHER PUBLICATIONS

Luo et al., Poster Session—"Enhancing Chinese Tone Recognition by Manipulating Amplitude Contour: Implications for Cochlear Implants", 2003 Conference on Implantable Auditory Prostheses, 23 pages, Aug. 2003.

Loizou, "Signal-Processing Techniques for Cochlear Implants," *IEEE Engineering in Medicine and Biology*, vol. 18, No. 3, pp. 34-46, May 1999.

Wilson et al., "Better Speech Recognition with Cochlear Implants," *Nature*, vol. 352, pp. 236-238, Jul. 1991.

United States Patent and Trademark Office, Office Action dated Feb. 2, 2011, pertaining to U.S. Appl. No. 12/420,179, 22 pages.

Sunstein Kann Murphy & Timbers LLP, Response to Office Action dated Feb. 2, 2011, pertaining to U.S. Appl. No. 12/140,179, 15 pages.

United States Patent and Trademark Office, Office Action dated Oct. 18, 2011, pertaining to U.S. Appl. No. 12/140,179, 11 pages.

International Searching Authority, International Search Report—International Application No. PCT/US09/39857 dated May 14, 2009, together with the Written Opinion of the International Searching Authority, 9 pages.

International Searching Authority, International Search Report—International Application No. PCT/US2008/069799—dated Nov. 3, 2008, together with the Written Opinion of the International Searching Authority, 14 pages.

\* cited by examiner

First Trace: Broadband signal b(t), band pass filtered within [100 Hz - 400 Hz]

Second Trace: Half wave rectified version of b(t)

Third Trace: Stimulation sequence at 5 kpulses/sec

ELECTRICAL NERVE STIMULATION WITH BROAD BAND LOW FREQUENCY FILTER

CROSS REFERENCE TO RELATED APPLICATIONS

This application is a continuation of U.S. patent application Ser. No. 12/171,857 is now U.S. Pat. No. 8,639,359, filed Jul. 11, 2008, which in turn claims priority from U.S. Provisional Patent Application 60/949,649, filed Jul. 13, 2007. Each of the above-described applications is hereby incorporated herein by reference in its entirety.

FIELD OF THE INVENTION

The present invention relates to electrical nerve stimulation, and more particularly, to a cochlear implant system that includes a broad band low frequency filter associated with a stimulation electrode.

BACKGROUND ART

Cochlear implants and other inner ear prostheses are one option to help profoundly deaf or severely hearing impaired persons. Unlike conventional hearing aids that just apply an amplified and modified sound signal; a cochlear implant is based on direct electrical stimulation of the acoustic nerve. Typically, a cochlear implant stimulates neural structures in the inner ear electrically in such a way that hearing impressions most similar to normal hearing are obtained.

FIG. 1 shows a section view of an ear with a typical cochlear implant system. A normal ear transmits sounds through the outer ear 101 to the eardrum 102, which moves the bones of the middle ear 103, which in turn excites the cochlea 104. The cochlea 104 includes an upper channel known as the scala vestibuli 105 and a lower channel known as the scala tympani 106, which are connected by the cochlear duct 107. In response to received sounds transmitted by the middle ear 103, the fluid filled scala vestibuli 105 and scala tympani 106 function as a transducer to transmit waves to generate electric pulses that are transmitted to the cochlear nerve 113, and ultimately to the brain. Frequency processing seems to change in nature from the basal region of the cochlea, where the highest frequency components of a sound are processed, to the apical regions of the cochlea, where the lowest frequencies are analyzed.

Some persons have partial or full loss of normal sensorineural hearing. Cochlear implant systems have been developed to overcome this by directly stimulating the user's cochlea 104. A typical cochlear prosthesis essentially includes two parts: the speech processor and the implanted stimulator 108. The speech processor (not shown in FIG. 1) typically includes a microphone, a power supply (batteries) for the overall system and a processor that is used to perform signal processing of the acoustic signal to extract the stimulation parameters. In state-of-the art prostheses, the speech processor is a behind-the-ear (BTE-) device. The implanted stimulator generates the stimulation patterns and conducts them to the nerve tissue by means of an electrode array 110 which usually is positioned in the scala tympani in the inner ear. The connection between speech processor and stimulator is usually established by means of a radio frequency (RF-) link. Note that via the RF-link both stimulation energy and stimulation information are conveyed. Typically, digital data transfer protocols employing bit rates of some hundreds of kBit/s are used.

One example of a standard stimulation strategy for cochlear implants is called "Continuous-Interleaved-Sampling strategy" (CIS), which was developed by B. Wilson (see, for example, Wilson B S, Finley C C, Lawson D T, Wolford R D, Eddington D K, Rabinowitz W M, "Better speech recognition with cochlear implants," Nature, vol. 352, 236-238, July 1991, incorporated herein by reference in its entirety). Signal processing for CIS in the speech processor typically involves the following steps:
1. Splitting up of the audio frequency range into spectral bands by means of a filter bank,
2. Envelope detection of each filter output signal,
3. Instantaneous nonlinear compression of the envelope signal (map law), and
4. Adaptation to thresholds (THR) and most comfortable loudness (MCL) levels According to the tonotopic organization of the cochlea, each stimulation electrode in the scala tympani is associated with a band pass filter of the external filter bank. For stimulation, symmetrical biphasic current pulses are applied. The amplitudes of the stimulation pulses are directly obtained from the compressed envelope signals (step (3) of above). These signals are sampled sequentially, and the stimulation pulses are applied in a strictly non-overlapping sequence. Thus, as a typical CIS-feature, only one stimulation channel is active at one time. The overall stimulation rate is comparatively high. For example, assuming an overall stimulation rate of 18 kpps, and using an 12 channel filter bank, the stimulation rate per channel is 1.5 kpps. Such a stimulation rate per channel usually is sufficient for adequate temporal representation of the envelope signal.

The maximum overall stimulation rate is limited by the minimum phase duration per pulse. The phase duration cannot be chosen arbitrarily short, because the shorter the pulses, the higher the current amplitudes have to be to elicit action potentials in neurons, and current amplitudes are limited for various practical reasons. For a 12 channel system with an overall stimulation rate of 18 kpps, the phase duration is 27 µs, which is at the lower limit.

CIS essentially represents envelope information in the individual channels. Temporal cues, e.g., the variations of the envelope signals with the pitch frequency, are presented to some extent. With a Channel Specific Sampling Sequences (CSSS) concept (see, for example, U.S. Pat. No. 6,594,525, "Electrical nerve stimulation based on channel specific sampling sequences," incorporated herein by reference in its entirety) the amount of temporal information is significantly increased. Temporal variations of the band pass output signals (sometimes designated as "temporal fine structure information") is represented in the lower frequency range, typically up to about 1 kHz. So a typical stimulation setting may include a mixture of low frequency CSSS channels and high frequency CIS channels. For each CSSS channel, a specific normalized sequence of ultra-high rate stimulation pulses is defined. For stimulation, the zero crossing of the associated band pass filter output is detected, and each zero crossing triggers such a predefined sequence, whereby the sequence is weighted with a factor derived from the instantaneous envelope of the band pass output. Thus, both the envelope and the temporal fine time information is represented in a CSSS stimulation sequence.

To enable a sufficiently high temporal resolution for CSSS, supporting concepts such as "Channel Interaction Compensation (CIC)" for simultaneous stimulation (see, for example, U.S. Pat. No. 6,594,525, entitled "Electrical Nerve Stimulation Based on Channel Specific Sampling Sequences," incorporated by reference in its entirety) or the "Selected Group (SG)" algorithm (see, for example, U.S. Patent Application Publication No. 20050203589, entitled "Electrical Stimulation of the Acoustic Nerve Based on Selected Groups," incorporated herein by reference in its entirety) may be utilized.

However, spatial channel interaction may cause distributions of electrical potentials, which could lead to unintentional hearing impressions. For example, let two neighboring stimulation electrodes 1 and 2 generate sequences with CSSS repetition rates of 100 Hz and 200 Hz, respectively. Because of spatial channel interaction, the 200 Hz sequence will distort the 100 Hz sequence at the position close to electrode 1, and could, e.g., lead to a 200 Hz hearing impression (octave failure). Vice versa, the 100 Hz sequence will distort the 200 Hz sequence in the vicinity of electrode 2 and could cause an additional 100 Hz tone which is could be audible. The amount of mutual distortion may depend on the exact phase relationship between the two sequences, and the channel interaction.

SUMMARY OF THE INVENTION

In accordance with one embodiment of the invention, a method of generating electrode stimulation signals for an implanted multi-channel electrode array of a cochlear implant is presented. The method includes processing an acoustic audio signal with a bank of filters. Each filter in the bank of filters is associated with at least one channel having an electrode. The bank of filters includes a first band pass filter that produces a broadband signal b(t) with frequencies that substantially cover at least one of a pitch frequency range of 100 Hz to 400 Hz and a first format range of 400 Hz-1000 Hz. At least one electrode associated with the first band pass filter is activated with electrode stimulation signals based, at least in part, on the broadband signal b(t).

In accordance with related embodiments of the invention, the at least one electrode may be positioned in an apical area of the cochlea. Only one electrode may be associated with the first band pass filter. Alternatively, at least two electrodes may be associated with the first band pass filter. The at least two electrodes may be activated simultaneously, using for example, sign correlated pulses. The at least two electrodes may be activated simultaneously using the same electrode stimulation signal. Activating the at least two electrodes may include stimulating the entire apical area within the cochlea.

In accordance with further related embodiments of the invention, the method may further include activating at least one electrode associated with one or more filters other than the first band pass filter, the one or more filters producing signals having higher frequencies than broadband signal b(t). The one or more filters may produce signals having only higher frequencies than broadband signal b(t). Activating at least one electrode associated with one or more filters other than the first band pass filter may include using a Continuous-Interleaved-Sampling strategy (CIS) and/or using Channel Interaction Compensation (CIC).

In accordance with still further related embodiment of the invention, the method may further include using a Selected Group (SG) algorithm. At least one electrode associated with the first band pass filter may be positioned at a predetermined spatial distance from other electrodes in the multi-channel electrode array so as to substantially avoid channel interaction. The broadband signal b(t) may be substantially limited to frequencies lower than 400 Hz. The broadband signal b(t) may be substantially limited to frequencies lower than 1000 Hz.

In accordance with another embodiment of the invention, a method of generating electrode stimulation signals for an implanted electrode array is presented. The method includes providing a bank of filters. Each filter is associated with at least one channel having an electrode. Furthermore, each filter is associated with a band of audio frequencies so as to generate a set of band pass signals. An acoustic audio signal is processed with the bank of filters. For each channel's electrode, stimulation information is extracted from their associated band pass signal to generate a set of stimulation event signals defining electrode stimulation signals. The electrode stimulation signals are developed into a set of output electrode pulses to the electrodes in the implanted electrode array. Providing the bank of filters includes determining the filters and associated bandpass signals so as to avoid low frequency channel interaction between electrodes.

In accordance with related embodiments of the invention, the pitch frequency range of 100 Hz to 400 Hz a may be covered by a single band pass filter in the bank of filters. The first format range of 400 Hz to 1000 Hz may be covered by a single band pass filter in the bank of filters. A single band pass filter in the bank of filters may cover a pitch frequency range of 100 Hz to 1000 Hz.

In accordance with another embodiment of the invention, a cochlear implant system includes a multi-channel electrode array having a plurality of stimulation electrodes for stimulating audio nerve tissue with the electrode stimulation signals. A preprocessor processes an acoustic audio signal, the processor including a bank of filters. Each filter in the bank of filters is associated with at least one channel having an electrode. The bank of filters includes a first band pass filter that produces a broadband signal b(t) with frequencies that substantially cover at least one of a pitch frequency range of 100 Hz to 400 Hz and a first format range of 400 Hz-1000 Hz. A stimulation module activates at least one electrode associated with the first band pass filter with electrode stimulation signals based, at least in part, on the broadband signal b(t).

In accordance with related embodiments of the invention, only one electrode may be associated with the first band pass filter. Alternatively, at least two electrodes may be associated with the first band pass filter. The stimulation module may activate the at least two electrodes simultaneously using the same electrode stimulation signal.

In accordance with further related embodiments of the invention, the filter bank may include at least one electrode associated with one or more filters other than the first band pass filter, with the one or more filters producing signals having higher frequencies than broadband signal b(t). The one or more filters may produce signals having only higher frequencies than broadband signal b(t).

In accordance with still further related embodiments of the invention, the stimulation module may use a Continuous-Interleaved-Sampling strategy (CIS) or Channel Interaction Compensation (CIC) to activate the at least one electrode associated with one or more filters other than the first band pass filter.

In accordance with yet further related embodiments of the invention, a Selected Group (SG) algorithm may be used. At least one electrode associated with the first band pass filter may be positioned at a spatial distance from other electrodes in the multi-channel electrode array so as to substantially avoid channel interaction. The broadband signal b(t) may be substantially limited to frequencies lower than 400 Hz. The broadband signal b(t) may be substantially limited to frequencies lower than 1000 Hz.

BRIEF DESCRIPTION OF THE DRAWINGS

The foregoing features of the invention will be more readily understood by reference to the following detailed description, taken with reference to the accompanying drawings, in which.

DETAILED DESCRIPTION OF THE INVENTION

In illustrative embodiments, a cochlear implant system and method provides a single, or minimal number of, (broadband) signals that include temporal fine structure information, such that distortion between competing neighboring channels containing temporal fine structure information are avoided. Details are discussed below.

Figure 1:
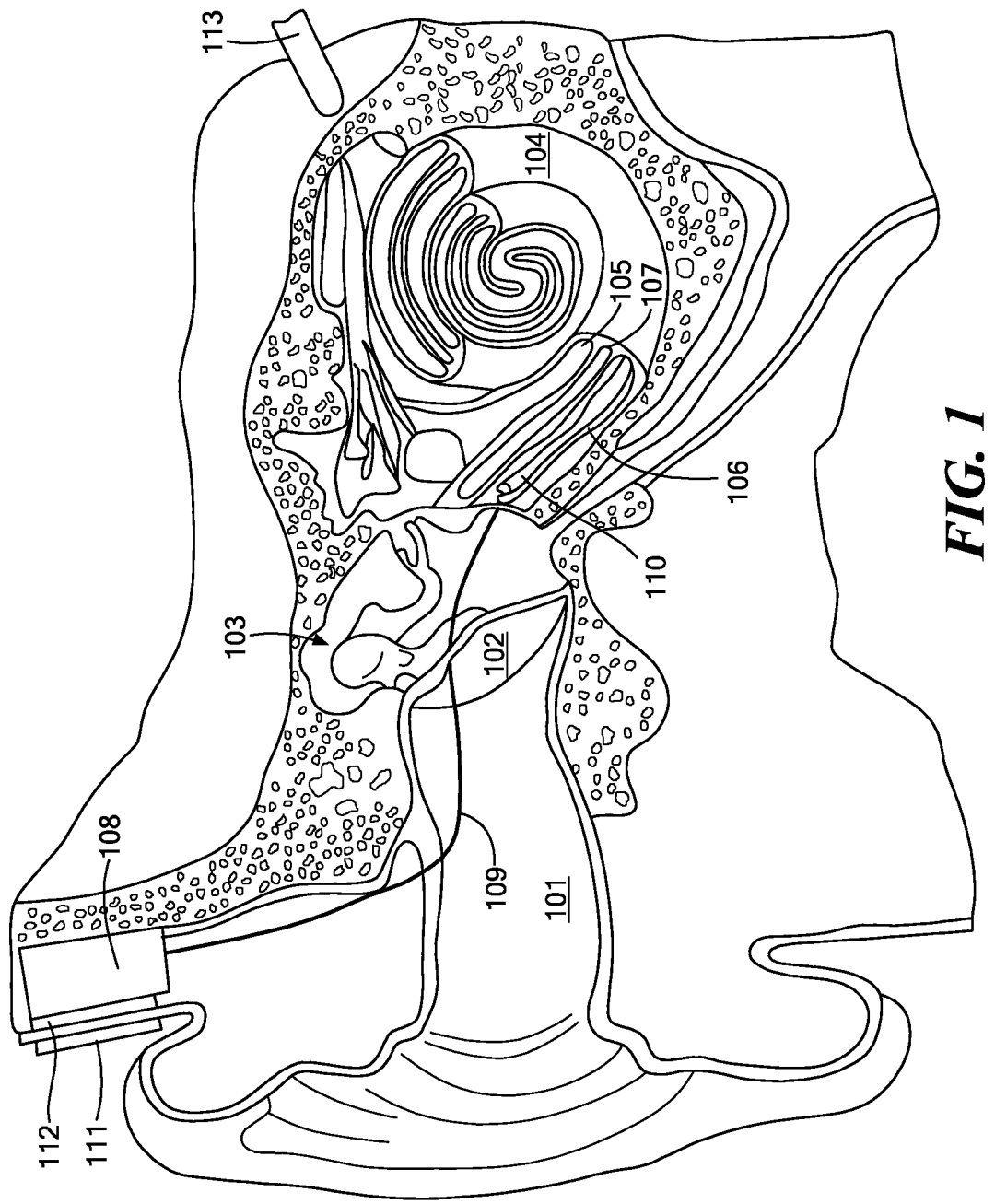
FIG. 1 shows a section view of an ear with a typical cochlear implant system.
Figure 2:
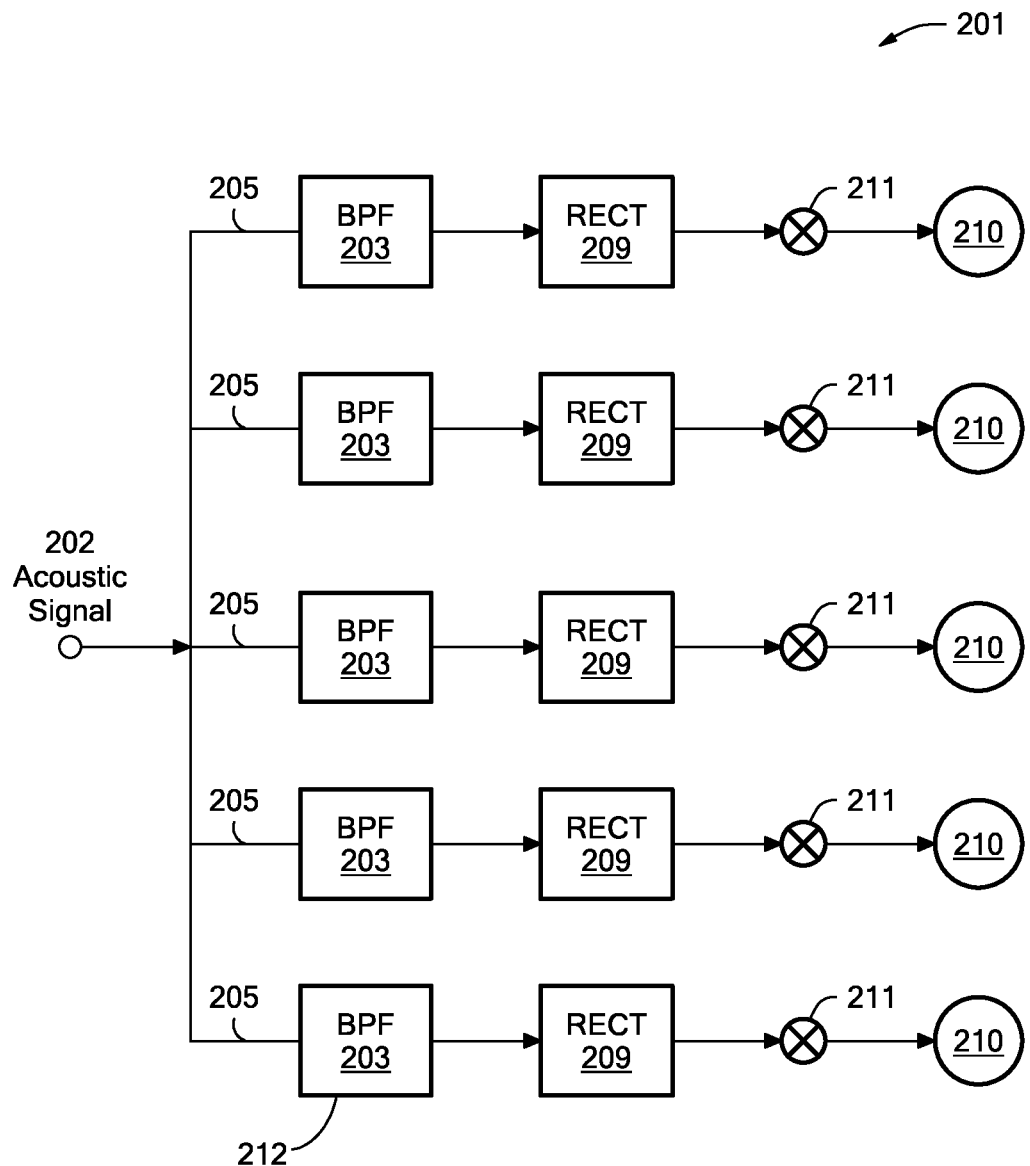
FIG. 2 shows shows a cochlear implant system 201, in accordance with one embodiment of the invention.

FIG. 2 shows a cochlear implant system 201, in accordance with one embodiment of the invention. As described above, the cochlear implant system 201 may have two parts; the external speech processor and the implanted stimulator 105 (see FIG. 1). The system 201 may be implemented, at least in part, by a controller integrated into the speech processor and/or stimulator 105. The controller may include, without limitation, a circuit and/or a processor that may be pre-programmed or configured to be loaded with an appropriate software program.

The cochlear implant system 201 includes a bank of filters 203, which may be implemented, without limitation, in the speech processor. Each filter 203 is associated with a band of audio frequencies so as to generate a set of band pass signals, with each band pass signal corresponding to the band of frequencies associated with one of the filters.

Each filter is associated with at least one channel 205 having an electrode 207. Each channel 205 may further include, without limitation, a half-wave rectifier 209, a sampling module 211, envelope detector, and/or a compressor. Illustratively, and without limitation, an acoustic audio signal 202 passing through each channel may thus be filtered to create a band pass signal, rectified, and sampled to, at least in part, create an electrode stimulation signal that is then provided to channel's associated electrode 210. Typically, the basic stimulation waveform is, without limitation, a symmetrical, biphasic pulse. The electrodes may be arranged in a monopolar configuration in which a remote ground electrode is used, or in a bipolar configuration wherein each active electrode has a corresponding reference electrode.

In illustrative embodiments of the invention, the bank of filters 203 includes a band pass filter 212 that provides a broadband signal b(t) covering a predetermined low frequency range. In various embodiments, the broadband signal b(t) is the only signal in the filter array associated with temporal fine structure information (typically associated with frequencies ≤1000 Hz), with minimal amount of filter roll off from other filters in the bank generally acceptable in various embodiments. The broadband frequency range may cover, without limitation, the pitch frequency range, typically 100 Hz to 400 Hz. In another embodiment, the broadband frequency range may cover the range of the first formant, typically 400 Hz to 1000 Hz. In yet another embodiment, the broadband frequency range covers the range of the pitch plus the first formant, typically 100 Hz to 1000 Hz.

The half wave rectified version of b(t) is sampled with a rate typically between 5-10 kHz. Similar to CIS, each sample is used, at least in part, to define the amplitude of a stimulation pulse. Typically, each sample value may be compressed (non-linear instantaneous compression, map law) and then adapted to the threshold and most comfortable loudness requirements of the patient. By presenting only one broadband signal that includes temporal fine structure information, distortions between competing neighboring channels containing temporal fine structure information are thus avoided.

The broadband signal b(t) may be used, without limitation, in combination with other CIS channels. To enable a sufficiently high temporal resolution to represent the broadband signal b(t) in combination with, for example, CIS channels, supporting concepts such as the "Channel Interaction Compensation (CIC)" or "Selected Group (SG)" algorithm may be utilized. Using CIC, amplitudes of the electrode stimulation pulses (which may be, without limitation simultaneously activated, sign correlated pulses) are calculated by taking into account parameters of spatial channel interaction reflecting geometric overlapping of electrical fields from each electrode. Generally, using the SG algorithm, electrodes with high spatial channel interaction usually are selected to establish a "Selected Group." Within a "Selected Group," stimulation pulses that are masked by spatial channel interaction are detected based on a simple "Maximum-Amplitude" criterion, and these pulses are not applied. Therefore for each stimulation cycle, a number of electrodes with the highest amplitudes (the number is programmable) within a "Selected Group" are detected before stimulation. Stimulation of only these electrodes is performed during one particular stimulation cycle, and this stimulation can be sequential or simultaneous. Members of a selected group should have sufficient spatial channel interaction, so that cochlear regions get sufficient stimulation. Algorithms used in providing the electrode stimulation signals may be implemented using a circuit and/or processor with is pre-programmed or configured to be loaded with an appropriate software program.

Figure 3A:
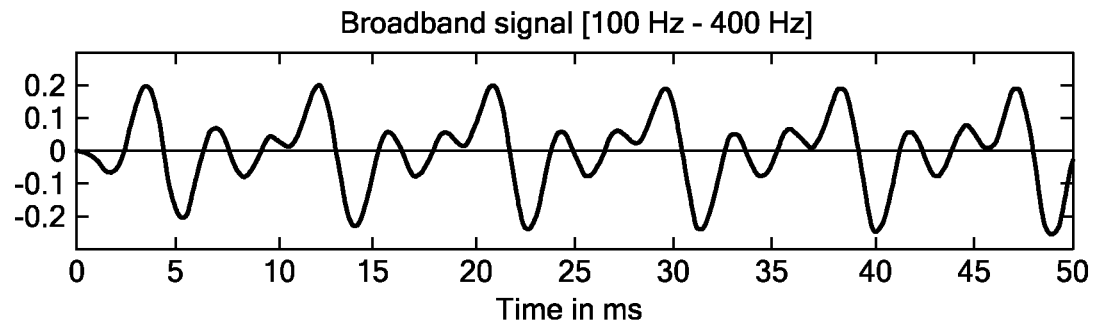
FIG. 3A shows a broadband signal filtered in a range [100 Hz-400 Hz], in accordance with one embodiment of the invention.
Figure 3B:
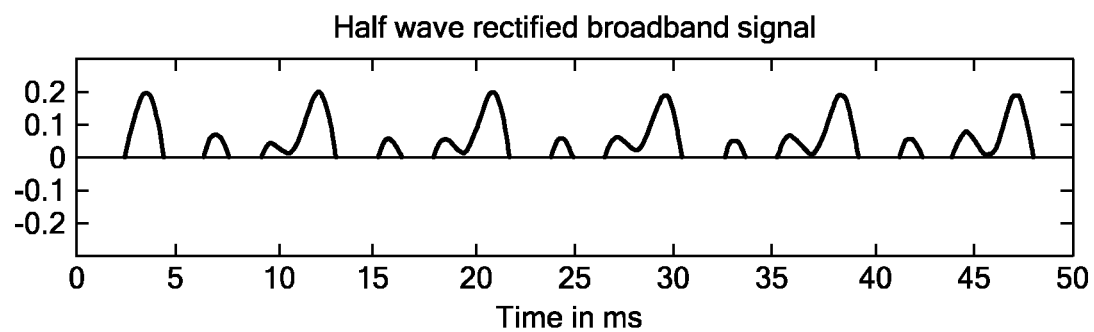
FIG. 3B shows the half wave rectified version of the broadband signal of FIG. 3A, in accordance with one embodiment of the invention.
Figure 3C:
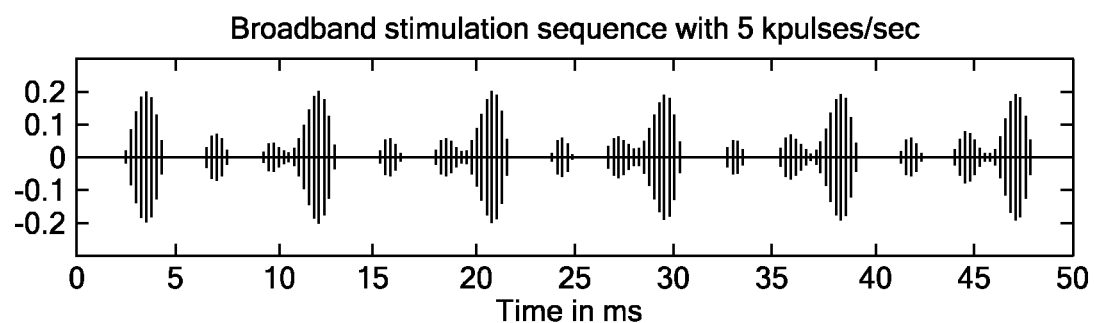
FIG. 3C shows the half wave rectified version of the broadband signal sampled at a rate of about 5 kHz, in accordance with one embodiment of the invention.

An illustrative example of the processing associated with the broadband signal is presented in FIGS. 3A-C, in accordance with one embodiment of the invention. FIG. 3A shows a broadband signal, filtered in a range [100 Hz-400 Hz]. FIG. 3B shows the half wave rectified version of the broadband signal. FIG. 3C shows the half wave rectified version of the broadband signal sampled at a rate of about 5 kHz, where each vertical line represents one stimulation pulse. Note that here for illustration, instantaneous compression and Adaptation to thresholds (THR) and most comfortable loudness (MCL) levels are omitted.

In accordance with one embodiment of the invention, the resulting broadband sequence may be applied to one apical low frequency channel and associated electrode. The overall stimulation configuration then consists of this low frequency broadband channel and the CIS channels in the higher frequency ranges. The CIS channels may substantially address frequencies that are only higher than those associated with the broadband sequence.

In accordance with another embodiment of the invention, the resulting broadband sequence may be applied to one apical low frequency channel and associated electrode, and a particular spatial distance to the first neighboring CIS channel is maintained to substantially reduce effects due to channel interaction between the broadband channel and the CIS channels. For example, one or more electrodes may be switched inactive.

In accordance with still another embodiment of the invention, the broadband sequence may be applied to several apical low frequency channels and associated electrodes simultaneously, so that the whole apical area within the cochlea is stimulated by only one sequence.

In accordance with yet another embodiment of the invention, the broadband sequence may be applied to several apical low frequency channels simultaneously, and a particular spatial distance to the first neighboring CIS channel is maintained. For example, one or more electrodes may be switched inactive.

Embodiments of the invention may be implemented in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

The described embodiments of the invention are intended to be merely exemplary and numerous variations and modifications will be apparent to those skilled in the art. All such variations and modifications are intended to be within the scope of the present invention as defined in the appended claims.

What is claimed is:

1. A method of generating electrode stimulation signals for an implanted multi-channel electrode array of a cochlear implant, the method comprising:
   processing an acoustic audio signal with a bank of filters, each filter in the bank of filters associated with at least one channel having an electrode, the bank of filters including a first band pass filter that produces a broadband signal b(t); and
   sampling the broadband signal b(t) while preserving temporal fine structure information associated with b(t);
   activating at least one electrode associated with the first band pass filter with electrode stimulation signals based, at least in part, on the sampled broadband signal b(t) such that the temporal fine structure is provided; and
   activating at least one electrode associated with one or more filters other than the first band pass filter, wherein activating at least one electrode associated with one or more filters other than the first band pass filter includes using a Continuous-Interleaved-Sampling strategy (CIS).

2. The method according to claim 1, wherein the broadband signal b(t) is substantially limited to frequencies lower than 400 Hz.

3. The method according to claim 2, wherein the broadband signal b(t) is further substantially limited to frequencies greater than 100 Hz.

4. The method according to claim 1, wherein the broadband signal b(t) is substantially limited to frequencies lower than 1000 Hz.

5. The method according to claim 4, wherein the broadband signal b(t) is further substantially limited to frequencies greater than 100 Hz.

6. The method according to claim 1, wherein sampling the broadband signal b(t) is at a sampling rate between 5-10 kHz.

7. The method according to claim 1, wherein the one or more filters other than the first band pass filter produce signals having only higher frequencies than broadband signal b(t).

8. The method according to claim 6, wherein activating at least one electrode associated with first band pass filter includes using each sample of the sampled broadband signal b(t) to define the amplitude of a stimulation pulse.

9. The method according to claim 1, further comprising using Channel Interaction Compensation (CIC).

10. The method of claim 1, further comprising using a Selected Group (SG) algorithm.

11. The method according to claim 1, further comprising positioning the at least one electrode associated with the first band pass filter at a predetermined spatial distance from other electrodes in the multi-channel electrode array so as to substantially avoid channel interaction.

12. The method according to claim 1 further including performing half wave rectification on b(t) prior to sampling.

13. The method according to claim 1, further comprising performing compression on the sampled broadband signal b(t) prior to activating the at least one electrode.

14. The method according to claim 1, further comprising adapting the sampled broadband signal b(t) to threshold and most comfortable loudness levels associated with a user of the cochlear implant prior to activating the at least one electrode.

15. A cochlear implant system comprising:
   a multi-channel electrode array having a plurality of stimulation electrodes for stimulating audio nerve tissue with the electrode stimulation signals,
   a processor for processing an acoustic audio signal, the processor including a bank of filters, each filter in the bank of filters associated with at least one channel having an electrode, the bank of filters including a first band pass filter that produces a broadband signal b(t);
   a sampling module for sampling the broadband signal b(t) while preserving temporal fine structure information associated with b(t); and
   a stimulation module for activating at least one electrode associated with the first band pass filter with electrode stimulation signals based, at least in part, on the sampled broadband signal b(t) such that the temporal fine structure is provided, wherein the stimulation module uses a Continuous-Interleaved-Sampling strategy (CIS) to activate the at least one electrode associated with one or more filters other than the first band pass filter.

16. The system according to claim 15, wherein the broadband signal b(t) is substantially limited to frequencies lower than 400 Hz.

17. The system according to claim 16, wherein the broadband signal b(t) is further substantially limited to frequencies greater than 100 Hz.

18. The system according to claim 15, wherein the broadband signal b(t) is substantially limited to frequencies lower than 1000 Hz.

19. The system according to claim 18, wherein the broadband signal b(t) is further substantially limited to frequencies greater than 100 Hz.

20. The system according to claim 15, wherein sampling the broadband signal b(t) is at a sampling rate between 5-10 kHz.

21. The system according to claim 20, wherein activating at least one electrode associated with first band pass filter includes using each sample of the sampled broadband signal b(t) to define the amplitude of a stimulation pulse.

22. The system according to claim 15, wherein the one or more filters other than the first band pass filter produce signals having only higher frequencies than broadband signal b(t).

23. The system according to claim 15, further comprising using Channel Interaction Compensation (CIC).

24. The system of claim 15, further comprising using a Selected Group (SG) algorithm.

25. The system according to claim 15, further comprising positioning the at least one electrode associated with the first band pass filter at a predetermined spatial distance from other electrodes in the multi-channel electrode array so as to substantially avoid channel interaction.

26. The system according to claim 15, further including a half-wave rectifier for performing half wave rectification on b(t) prior to sampling.

27. The system according to claim 15, further comprising a signal processor for performing compression on the sampled broadband signal b(t) prior to activating the at least one electrode.

28. The method according to claim 15, further comprising a signal processor for adapting the sampled broadband signal b(t) to threshold and most comfortable loudness levels associated with a user of the cochlear implant prior to activating the at least one electrode.

* * * * *